United States Patent
Kanbar et al.

(10) Patent No.: US 8,486,016 B2
(45) Date of Patent: Jul. 16, 2013

(54) APPARATUS AND METHOD FOR SHIELDING A HYPODERMIC NEEDLE AFTER USE

(75) Inventors: Maurice S. Kanbar, San Francisco, CA (US); Albert Kolvites, San Mateo, CA (US)

(73) Assignee: Maurice S. Kanbar Revocable Trust, San Francisco, CA (US)

( * ) Notice: Subject to any disclaimer, the term of this patent is extended or adjusted under 35 U.S.C. 154(b) by 0 days.

(21) Appl. No.: 13/294,112

(22) Filed: Nov. 10, 2011

(65) Prior Publication Data

US 2013/0123698 A1     May 16, 2013

(51) Int. Cl.
    *A61M 5/00*     (2006.01)
(52) U.S. Cl.
    USPC ............ 604/111; 604/110; 604/192; 604/198
(58) Field of Classification Search
    CPC ..................... A61M 5/3271; A61M 5/3243
    USPC .................................. 604/110, 192, 198, 111
    See application file for complete search history.

(56) References Cited

U.S. PATENT DOCUMENTS

| | | |
|---|---|---|
| 4,573,976 A | 3/1986 | Sampson et al. |
| 4,695,274 A | 9/1987 | Fox |
| 4,731,059 A | 3/1988 | Wanderer et al. |
| 4,863,435 A | 9/1989 | Sturman et al. |
| 4,915,696 A | 4/1990 | Feimer |
| 4,921,490 A | 5/1990 | Spier et al. |
| 5,013,305 A | 5/1991 | Opie et al. |
| 5,092,851 A | 3/1992 | Ragner |
| 5,201,708 A | 4/1993 | Martin |
| 5,215,534 A | 6/1993 | De Harde et al. |
| 5,246,427 A | 9/1993 | Sturman et al. |
| 5,411,492 A | 5/1995 | Sturman et al. |
| 5,466,223 A * | 11/1995 | Bressler et al. ............... 604/110 |
| 2011/0082428 A1 | 4/2011 | Huang |
| 2011/0118674 A1 | 5/2011 | Doyle |
| 2011/0144594 A1 | 6/2011 | Sund et al. |
| 2011/0166526 A1 | 7/2011 | Kuracina et al. |
| 2011/0208124 A1 | 8/2011 | Rhad et al. |
| 2011/0208133 A1 | 8/2011 | Woehr et al. |

* cited by examiner

*Primary Examiner* — Laura Bouchelle
(74) *Attorney, Agent, or Firm* — Litts Law Firm (57) ABSTRACT

An apparatus for shielding a hypodermic needle after use may include a device adapted to accommodate a needle extending from an end thereof, a guard element coupled to the device, a lock element, and an indicator element. The guard element may slide axially with respect to the device and may include a slider portion and a shield portion. The shield portion may include an open slot to accommodate the needle. Upon sliding the guard element to a designated position, the lock element may automatically secure a position of the guard element relative to the device, such that the shield portion obstructs access to the needle tip. The indicator element may provide visual, audible, and/or tactile feedback to indicate that the lock element has been actuated to shield the needle tip.

32 Claims, 6 Drawing Sheets

APPARATUS AND METHOD FOR SHIELDING A HYPODERMIC NEEDLE AFTER USE

BACKGROUND

This invention relates to medical devices and, more particularly, to safety devices to prevent reuse of a hypodermic needle.

Hypodermic needles and syringes have long been used as a quick and easy way to transfer liquids into and out of the body. Indeed, the term "hypodermic" is derived from the Greek words "hypo", meaning under, and "derma", meaning skin. Appropriately, fluid (such as a drug or blood) may be drawn up into the barrel of the syringe by inserting a hollow needle associated with the syringe into the fluid, and pulling back a plunger residing within the barrel to create a vacuum. The fluid may be administered subcutaneously, or withdrawn subcutaneously and otherwise dispensed with, by pushing the plunger back into its original position. A user can determine exactly how much material is withdrawn or dispensed by reading the measuring marks on the side of the barrel.

Hypodermic needles are commonly used in medical, veterinary and laboratory fields, and are increasingly accessible to the general public. As a result, needlestick injuries arising from improperly disposed or maliciously discarded needles are a significant risk to professionals and non-professionals alike. Needlestick injuries can introduce into the body harmful materials or micro-organisms from the skin as a result of contaminants on the outside of the needle and/or within the needle bore. Of particular concern is the transmission of blood-borne pathogens, such as the hepatitis B virus ("HBV"), the hepatitis C virus ("HCV") and the human immunodeficiency virus ("HIV"), which causes Autoimmune Deficiency Syndrome ("AIDS").

Medical devices incorporating hypodermic needles thus typically include an overcap or other protective device that may be placed over the needle after it has been used. In theory, such a protective device prevents injury arising from later contact with contaminated portions of the needle and sharp needle tip. Although many design variations exist, however, protective devices are often difficult to manipulate, and the practice of affixing the overcap or other protective device over a used needle may itself render one susceptible to an accidental needlestick. In fact, the majority of accidental needlestickes occur when needles are being re-capped. Moreover, such overcaps or devices may be unreliable due to difficulty in distinguishing a hypodermic needle that has been properly secured from one that has not.

In view of the foregoing, what are needed are apparatus and methods to secure a hypodermic needle that are simple to use and manufacture, and provide reliable protection against needlestick injuries. Further what are needed are apparatus and methods that clearly indicate whether a hypodermic needle has been properly secured and is, therefore, safe to handle. Such apparatus and methods are disclosed and claimed herein.

BRIEF DESCRIPTION OF THE DRAWINGS

In order that the advantages of the invention will be readily understood, a more particular description of the invention briefly described above will be rendered by reference to specific examples illustrated in the appended drawings. Understanding that these drawings depict only typical examples of the invention and are not therefore to be considered limiting of its scope, the invention will be described and explained with additional specificity and detail through the use of the accompanying drawings, in which:

FIG. 1b is a side view of the apparatus of FIG. 1a;

FIG. 6a is a perspective view detailing an adapter element, track element, and lock element in accordance with certain embodiments;

FIG. 6b is a front view of the adapter element, track element, and lock element of FIG. 6a;

FIG. 6c is a side view of the adapter element, track element, and lock element of FIG. 6a;

FIG. 7b is a front view of the guard element of FIG. 7a;

FIG. 7c is a side view of the guard element of FIG. 7a;

DETAILED DESCRIPTION

The invention has been developed in response to the present state of the art, and in particular, in response to the problems and needs in the art that have not yet been fully solved by currently available methods and apparatus to shield a hypodermic needle after use. Accordingly, the invention has been developed to provide a novel apparatus and method for shielding a hypodermic needle that utilizes a sliding guard element to automatically lock the guard element in place and simultaneously indicate that the needle has been properly secured. The features and advantages of the invention will become more fully apparent from the following description and appended claims and their equivalents, and also any subsequent claims or amendments presented, or may be learned by practice of the invention as set forth hereinafter.

In one embodiment, an apparatus for shielding a hypodermic needle may include a device adapted to accommodate a needle extending from an end thereof, a guard element coupled to the device, a lock element, and an indicator element. The guard element may slide axially with respect to the device, and may include a slider portion and a shield portion. The shield portion may include an open slot to accommodate the needle. Upon sliding the guard element to a designated position, the lock element may automatically secure a position of the guard element relative to the device, such that the shield portion obstructs access to the needle tip. The indicator element may provide visual, audible, and/or tactile feedback to indicate that the lock element has been actuated to shield the needle tip.

It will be readily understood that the components of the present invention, as generally described and illustrated in the Figures herein, could be arranged and designed in a wide variety of different configurations. Thus, the following more detailed description of the embodiments of apparatus and methods in accordance with the present invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1A:
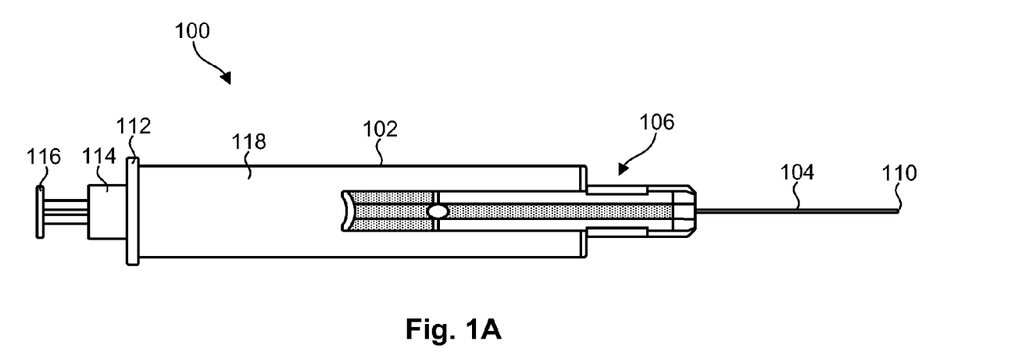
FIG. 1a is a top view of an apparatus for shielding a hypodermic needle in accordance with one embodiment of the invention.
Figure 1B:
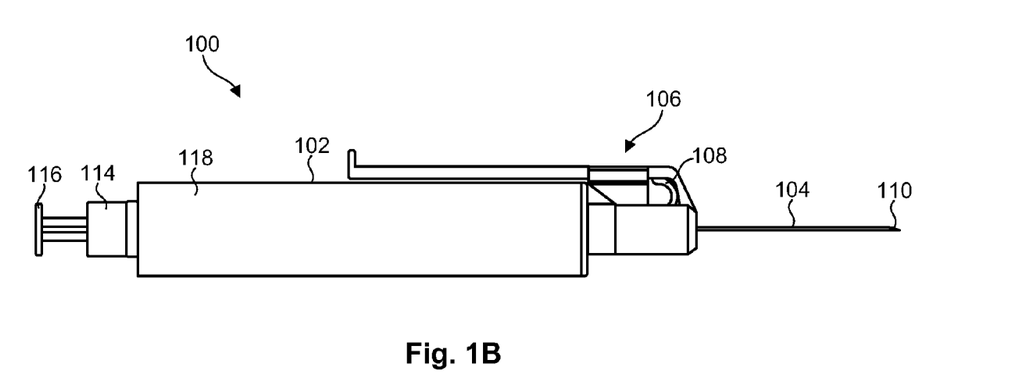

With reference now to FIGS. 1a and 1b, one embodiment of an apparatus 100 for securing a hypodermic needle 104 after use is illustrated. As previously discussed, most accidental needlestick injuries arise when an overcap or other protective device is applied over a needle 104 after use. Embodiments of the present invention may overcome this problem by enabling actuation of a guard element 106 without requiring significant manipulation or proximate contact between the user and the used needle 104. Further, embodiments of the invention may enable the guard element 106 to be automatically secured to obstruct access to the needle tip 110, and may provide an automatic indication that the guard element 106 is properly secured.

While the illustrated embodiments show a guard element 106 used in connection with a syringe 102, one skilled in the art will recognize that the guard element 106 and other features of the present invention may be used in connection with any device where protection from a used needle is desired. For example, certain embodiments of the invention may be implemented in connection with a surgical knife, an intravenous catheter assembly, a surgical instrument, or any other medical or surgical device known to those in the art.

As shown, a syringe 102 typically includes a cylindrical fluid chamber 118 formed of transparent, synthetic plastic material such as polyethylene, polypropylene, polystyrene or PVC. The syringe 102 may include indicia to measure a quantity of fluid contained in the chamber 118. A piston 114 having an outer circumference substantially corresponding to an inner circumference of the chamber 118 may be disposed therein to slide with respect to the chamber 118. In this manner, a user may manipulate the piston 114 via a handle 116 to admit or expel fluid from the chamber 118. A flange 112 may extend from an end of the syringe 102 to facilitate such manipulation.

A needle 104 may extend from the opposite end of the syringe 102 and may penetrate the skin to enable fluid to be subcutaneously introduced or withdrawn. The guard element 106 may be coupled to the syringe 102 and retained away from the needle tip 110 such that it does not interfere with the normal operation of the syringe 102 and needle 104. In one embodiment, for example, the guard element 106 may be retained between the syringe 102 and the needle 104 via an adapter element (not shown) or other device coaxially disposed with or otherwise coupled to the syringe 102 and needle 104. During operation, as discussed in more detail below, the guard element 106 may be actuated to slide axially with respect to the syringe 102 to obstruct access to the needle tip 110.

In certain embodiments, the guard element 106 may be configured to accommodate syringes 102 having any of several standard diameters and dimensions. Particularly, as discussed in more detail below, the guard element 106 may be formed to clear a substantially large-diameter syringe 102, while smaller-diameter syringes 102 may also be accommodated, albeit with increased distance between the guard element 106 and the outside surface of the syringe 102.

Figure 2:
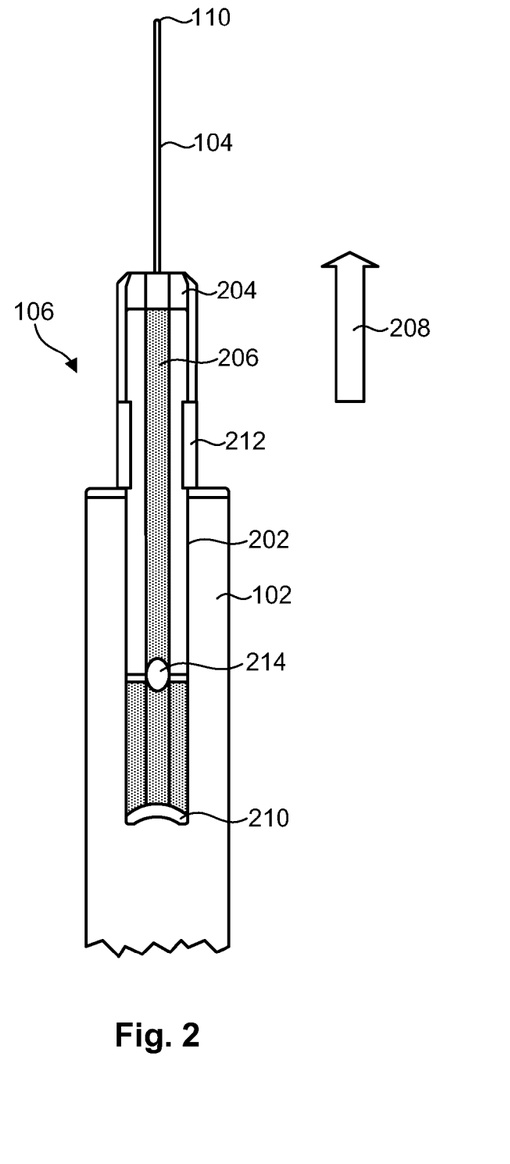
FIG. 2 is a top view of one embodiment of an apparatus for shielding a hypodermic needle showing the lock element in a "loaded" position prior to actuation.
Figure 3:
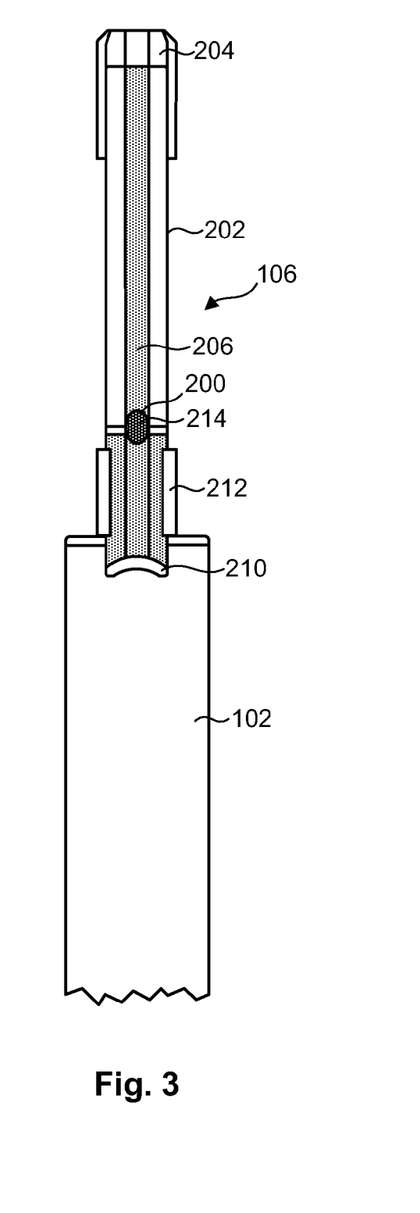
FIG. 3 is a top view of the apparatus of FIG. 2, illustrating the lock element in an actuated and locked position.

As shown in FIGS. 2 and 3, the guard element 106 may be actuated to safeguard the needle tip 110 after use. In certain embodiments, the guard element 106 may include a slider portion 202 and a shield portion 204. The shield portion 204 may be formed of a resilient, medical-grade synthetic plastic material such as polycarbonate, polypropylene, polystyrene, or the like. As discussed in more detail below, the shield portion 204 may include a cylindrical or barrel-like shape to substantially surround the needle 104, and may include an open slot (not shown) to facilitate manufacturing and assembly. Specifically, as discussed in more detail below, the open slot may receive the needle 104 into a central position relative to the barrel.

The slider portion 202 may include an elongate bar extending longitudinally from the shield portion 204. In some embodiments, the slider portion 202 and shield portion 204 may be coupled together, while in other embodiments the slider portion 202 and shield portion 204 may be integrally formed. A flange 210 may extend from a distal end of the slider portion 202 to facilitate sliding the guard element 106 in an axial direction 208 towards the needle tip 110 to secure the needle 104 after use.

The slider portion 202 may be constructed of a transparent, resilient material such as a medical-grade synthetic plastic material including, for example, polycarbonate, polypropylene, polystyrene, or the like. An aperture 214 may be provided through the slider portion 202 at a position substantially corresponding to an indicator element 200 when the guard element 106 is actuated to shield the needle 104, as discussed in more detail below.

In certain embodiments, a strip 206 of contrasting paint or the like may be applied to an underside or other portion of the slider portion 202 to facilitate visual feedback during operation of the guard element 106. Particularly, in one embodiment, a black strip 206 may be applied to the underside of the slider portion 202. The strip 206 may be centered with respect to the slider portion 202 and may have a length substantially corresponding thereto. The width of the strip 206 may vary along its length, such that the width is slightly less than the width of the slider portion 202 from its distal end to the aperture 214, and substantially corresponds to the width of the slider portion 202 from the position of the aperture 214 to the proximal end of the slider portion 202.

In this manner, as discussed in more detail below, a contrasting color (such as red) may be visible on either side of the strip 206 until the aperture 214 engages the indicator element 200, thereby providing a visual indication that the needle tip 110 has been secured. This visual feedback may be enhanced where the indicator element 200 includes another distinct color (such as green), visible only upon engagement of the aperture 214 with the indicator element 200.

As shown in FIG. 2, in the retracted position, the slider portion 202 may lie substantially adjacent to an outer surface of the syringe 102. The shield portion 204 may be retained to substantially surround the needle 104 at a position removed from the needle tip 110, so as to avoid interference with the usual operation of the syringe 102. During operation, the guard element 106 may be slid in an axial direction 208 towards the needle tip 110. Thus, as shown in FIG. 3, in the secure position, the slider portion 202 may be retained along the length of the needle 104, while the shield portion 204 may substantially surround the needle 104 and extend beyond the needle tip 110 to secure the needle. 104 after use.

Figure 4:
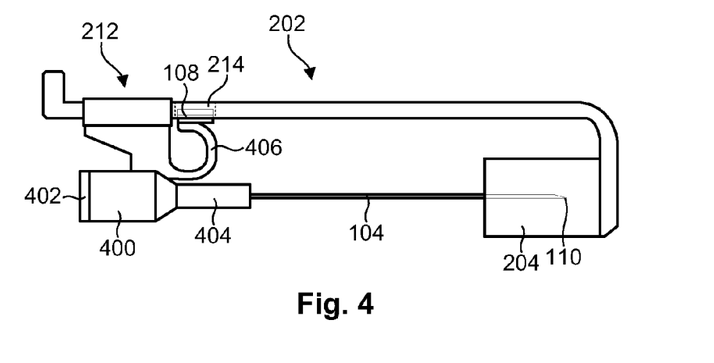
FIG. 4 is a side view of the guard element in an actuated position in accordance with embodiments of the invention.

Referring now to FIG. 4, an adapter element 400 may be provided to engage the open receptacle end of the syringe 102. In certain embodiments, a proximal end 402 of the adapter element 400 includes external features or threads to mate with internal features or threads on the inside surface of the syringe 102. For example, the adapter element 400 may be a Luer device, having standard Luer taper dimensions, as set forth in the International Organization for Standardization ("ISO") 594 standards. These standardized taper dimensions enable one or more Luer devices to be interconnected by male and female interlocking features. In other embodiments, the proximal end 402 of the adapter element 400 engages the open end of the syringe 102 via a press fit, or by any other means known to those in the art.

The distal end 404 of the adapter element 400 may retain the proximal end of the needle 104. In some embodiments, the distal end 404 of the adapter element 400 may taper with respect to its proximal end 402, conforming with standard Luer-lock style connectors. As discussed in more detail below with reference to FIG. 5, this shape may also enable the shield portion 204 of the guard element 106 to be retracted over the adapter element 400 and retained near its proximal end 402.

As shown in FIG. 4, some embodiments of an adapter element 400 may include a track element 212 extending laterally from therefrom. When the adapter element 400 is engaged with the open end of the syringe 102, the track element 212 may retain the slider portion 202 substantially adjacent to the outer surface of the syringe 102. Specifically, the track element 212 may provide a substantially planar track surface (not shown) and retaining sidewalls to enable the slider portion 202 to slide axially toward the needle tip 110, while maintaining the lateral orientation of the slider portion 202 relative to the syringe 102.

Figure 5:
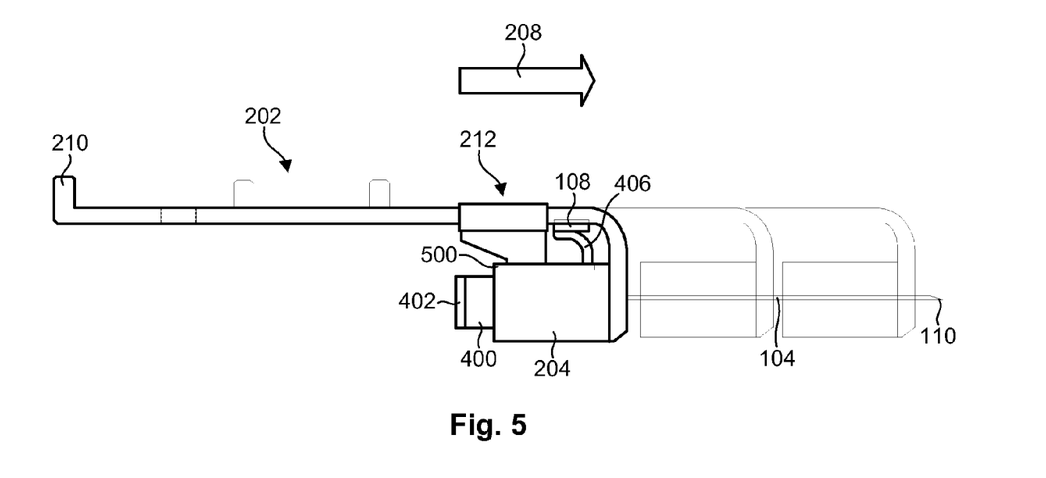
FIG. 5 is a side view of the guard element shown in a refracted position and in successive positions as it is actuated along the length of a needle.

Additionally, in some embodiments, a lock element 108 may be coupled to the track element 212 and may substantially correspond to the slider portion 202 of the guard element 106. In one embodiment, as shown in FIG. 5, a biasing member 406 couples the lock element 108 to the track element 212. The substantially rigid nature of the slider portion 202 in combination with the resilient nature of the biasing member 406 may maintain the lock element 108 in a "loaded" position until the guard member 106 is actuated.

Upon actuation, the slider portion 202 may slide in an axial direction 208 towards the needle tip 110. As a result, the aperture 214 disposed in the slider portion 202 may approach and eventually align with the "loaded" lock element 108. As shown in FIG. 4, the biasing member 406 may then release the lock element 108 to engage the aperture 214, thereby locking the position of the guard element 106 with respect to the syringe 102 and needle 104.

As illustrated in FIG. 5, the tight tolerance between the slider portion 202 and the track element 212 may facilitate linear movement of the guard element 106 with respect to the syringe 102 and needle 104. This tight tolerance may also enable the shield portion 204 of the guard element 106 to maintain close contact with the needle 104 along its length.

As discussed in more detail below, the shield portion 204 may include an open slot (not shown) to receive the needle 104. The slot may be configured to receive the needle 104 into a substantially central position with respect to the shield portion 204, while the shield portion 204 may substantially surround at least a portion of the outer surface of the needle 104. This configuration may ease manufacturing and assembly of the apparatus 100 with respect to a syringe 102 or other medical device. Specifically, this design may enable the shield portion 204 to simply fit over the needle 104 instead of requiring threading the needle 104 through the shield portion 204, or otherwise requiring substantial manipulation of the apparatus 100 with respect to the needle 104 for assembly.

In certain embodiments incorporating the track element 212 and lock element 108 illustrated in FIG. 5, the shield portion 204 may include a channel 500 integrated into a top surface thereof. The channel 500 may be formed to accommodate a cross-sectional profile of the track element 212 and biasing member 406, thereby enabling the guard element 106 to be retracted over the adapter element 400 without interference. In some embodiments, the slider portion 202 may include a detent or other feature to facilitate maintaining the guard element 106 in the retracted position, while requiring only minimal force to urge the guard element 106 forward to shield the needle tip 110.

Figures 6A, 6B, 6C:
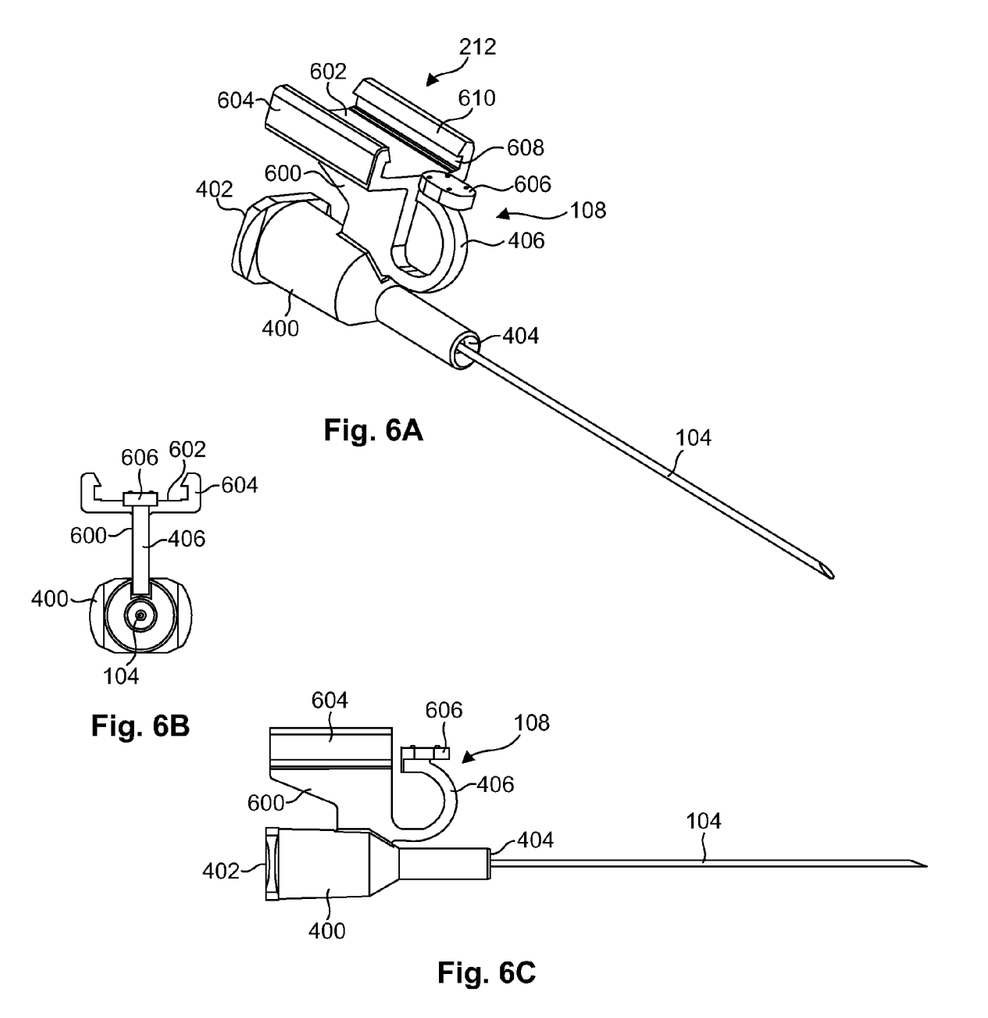

Referring now to FIGS. 6a-c, in some embodiments, the track element 212 may include a bracket 600 extending from the adapter element 400 and supporting a substantially planar track surface 602. As shown in FIG. 6b, the bracket 600 may include a substantially narrow profile to conform to the channel 500 of the shield portion 204, as discussed above. Further, the bracket 600 may include a height sufficient to avoid interference between the shield portion 204 and the substantially planar track surface 602 when the guard element 106 is in a retracted position. The height of the bracket 600 may further be selected to avoid interference between the substantially planar track surface 602 and the outer contour of the syringe 102.

The substantially planar track surface 602 may have a width equal to or greater than that of the slider portion 202, and may be oriented to guide the slider portion 202 in an axial direction relative to the syringe 102. Retaining sidewalls 604 may extend in a substantially perpendicular direction relative to the track surface 602 to maintain alignment between the slider portion 202 and the track surface 602. As shown in FIG. 6a, in some embodiments, the retaining sidewalls 604 may include lateral grooves 608 and/or lips 610 to maintain close contact between the slider portion 202 and the track surface 602. Nevertheless, the retaining sidewalls 604 may be sufficiently resilient to permit ease of manufacture by simply pressing the slider portion 202 onto the track element 212. Specifically, the application of downward pressure in this manner may enable slight outward deformation of the sidewalls 604 to receive the slider portion 202, which may then be retained by the lateral grooves 608 and/or lips 610.

In certain embodiments, the lock element 108 may be coupled to the bracket 600 of the track element 212. As discussed above, the lock element 108 may include a biasing member 406 having a projection 606 substantially corresponding to the size and shape of the aperture 214 disposed in the slider portion 202. In one embodiment, as shown in FIGS. 6a and 6b, one end of the biasing member 406 may be attached to a base of the bracket 600 such that the profile of the biasing member 406 substantially corresponds to the profile of the bracket 600. This may enable both the biasing member 406 and bracket 600 to be received into the channel 500 of the shield portion 204 in the retracted position.

As shown in FIG. 6c, the projection 606 of the lock element 108 may extend from an opposite end of the biasing member 406 such that the projection 606 is maintained at a level slightly above that of the track surface 602. Introduction of the slider portion 202 onto the track surface 602 may thus bias the projection 606 beneath the slider portion 202, placing the lock element 108 in a compressed or "loaded" position.

As one skilled in the art will recognize, any or all of the adapter element 400, track element 212, and lock element 108 may be separately formed and coupled together, or may be integrally formed.

Figure 7A:
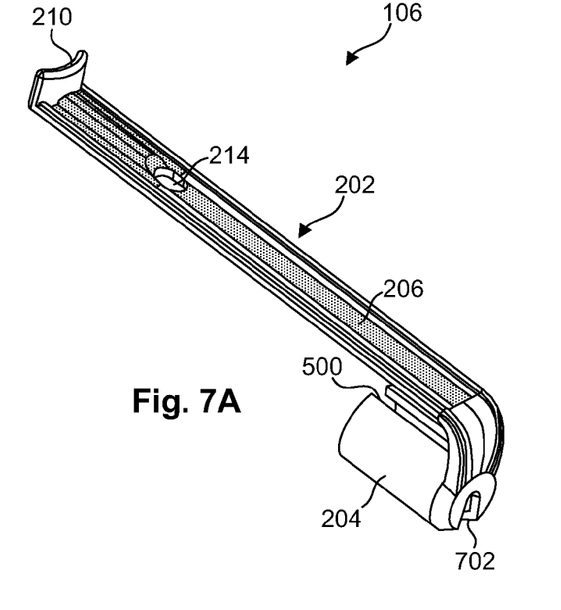
FIG. 7a is a perspective view of a guard element in accordance with certain embodiments of the invention.
Figure 7B:
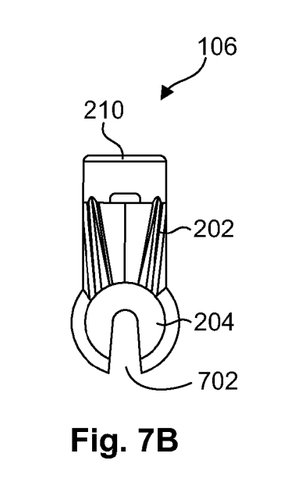
Figure 7C:
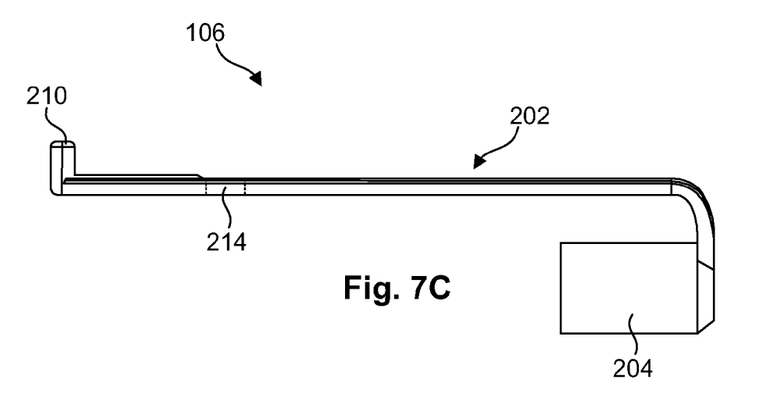

Referring now to FIGS. 7a-c, the guard element 106 may include a shield portion 204 coupled to a slider portion 202. The shield portion 204 may be substantially cylindrical and may incorporate an open or V-shaped slot 702 extending longitudinally along its axis. In this manner, the open end of the slot 702 may correspond to an outer surface of the shield portion 204.

The open end of the slot 702 may receive the needle 104 along its length. In this manner, the shield portion 204 may be quickly and easily positioned to substantially surround the needle 104, after which the tight tolerance between the slider portion 202 and the track element 212 may be utilized to quickly and easily transition the shield portion 204 to a position beyond the needle tip 110 to obstruct access thereto. This arrangement may reduce the risk of accidental needlesticks arising during application or assembly of the guard element 106 with respect to the needle 104.

The inside end of the slot 702 may substantially correspond to the center of the shield portion 204. Thus, upon application of the guard element 106, at least a portion of the length of the needle 104 may be retained substantially against the inside end of the slot 702. As mentioned above, the slider portion 202 may be urged in an axial direction toward the needle tip 110 to move the shield portion 204 linearly to prevent accidental contact with the tip 110 after its initial use.

The shield portion 204 may also include a narrow channel 500 extending substantially parallel to its axis and to the needle 104, when operative. The channel 500 may include dimensions sufficient to accommodate the track element 212 and/or lock element 108 when the shield portion 204 is retracted and retained over the adapter element 400.

The slider portion 202 may be coupled to the shield portion 204 such that the length of the slider portion 202 runs substantially parallel to the axis of the shield portion 204. As shown in FIGS. 7a and 7c, however, the slider portion 202 may be suspended with respect to the shield portion 204 to provide clearance for the outer contour of the syringe 102. As mentioned previously, the clearance provided may be sufficient to permit universal application of the guard element 106 to any of several standard sizes of syringe 102.

Figure 8A:
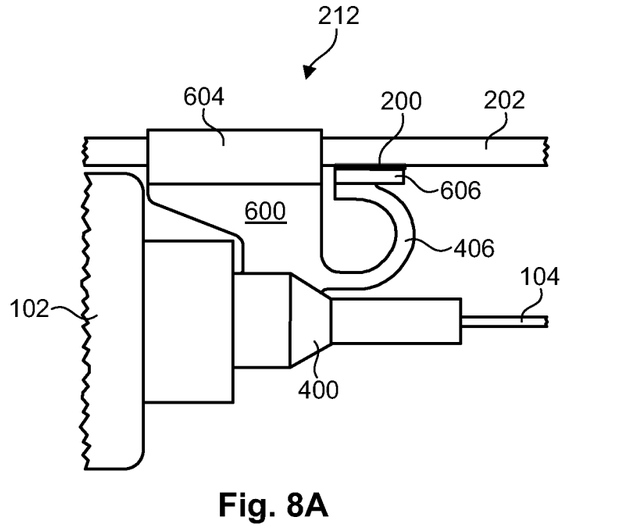
FIG. 8a is a side view of one embodiment of the guard element having the lock element and indicator element in a "loaded" position prior to actuation.
Figure 8B:
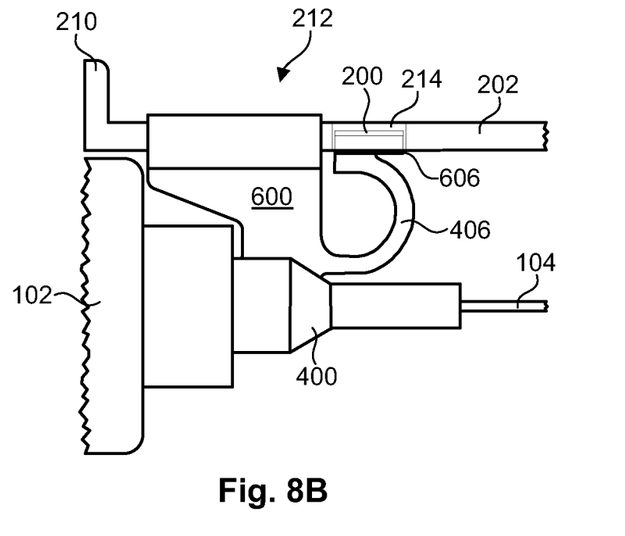
FIG. 8b is a side view of the guard element of FIG. 8a showing the lock element and indicator element actuated and locked.

Referring now to FIGS. 8a and 8b, an indicator element 200 may be provided to alert a user to whether the guard element 106 has been properly actuated and locked into a safety position. For example, in some embodiments, the indicator element 200 may include a layer of synthetic plastic, paint, or other material or substance known to those in the art to distinguish the indicator element 200 from the slider portion 202, the track element 212, and other features of the apparatus 100.

In certain embodiments, the indicator element 200 may include a colored tab or layer coupled to a top surface of the projection 606 of the lock element 108. The color of the indicator element 200 may be unique from the surrounding colors of the apparatus 100 to permit easy visual identification. The indicator element 200 may have a shape and size substantially conforming to that of the projection 606, such that the indicator element 200 and projection 606 may engage the aperture 214 of the slider portion 202 substantially simultaneously, as a unit.

In certain embodiments, engagement of the indicator element 200 and projection 606 with the aperture 214 of the slider portion 202 may also provide audible feedback in the form of a click, snap, or other sound or audible noise known to those in the art. In some embodiments, engagement of the aperture 214 may also provide tactile feedback in the form of an abrupt stop, distinguishing tactile patterns or features of the indicator element 200, or other tactile features or mechanisms known to those in the art.

In one embodiment, as shown in FIGS. 8a and 8b for example, the indicator element 200 may be a green tab affixed to conform to the projection 606. When the lock element 108 is in the "loaded" position, as shown in FIG. 8a, the projection 606 and attached indicator element 200 may be maintained in a substantially centered position beneath the level of the slider portion 202.

As discussed above, the slider portion 202 may be substantially transparent and, in some embodiments, may include a narrow strip 206 of contrasting (i.e. black) paint along its length. The dimensions of the strip 206 may permit an underlying color to show through the transparent edges of the slider portion 202, while obscuring view of the indicator element 200 centered beneath the slider portion 202. In certain embodiments, the track surface 602 of the track element 212 may be painted a distinct color (i.e. red), such that a user may distinguish that color along the edges of the slider portion 202 prior to actuation of the lock element 108.

Upon actuation of the lock element 108, the projection 606 and attached indicator element 200 may be thrust through the aperture 214 to both lock the guard element 106 in position relative to the syringe 102 and needle tip 110, and to indicate that the guard element 106 has been properly actuated and locked. As shown in FIG. 8b, the engagement of the projection 606 and indicator element 200 with the aperture 214 may provide visual feedback to a user by showing the contrasting (i.e. green) colored tab through the slider portion 202. The length of the slider portion 202 proximal to the aperture 214 may be painted a solid contrasting color (i.e. black), and may extend to the edges of the slider portion 202 to prevent any underlying color (i.e. red) from showing through after the lock element 108 has been actuated.

In the example set forth above, therefore, a user watching the slider portion 202 for visual feedback regarding whether the needle tip 110 is secure may perceive the following sequence. Initially, the slider portion 202 may be retracted against the syringe 102 or other medical device such that the user perceives the black strip 206 and red edges on opposing sides of the black strip 206. As discussed previously, the color red may be perceived as a result of the track surface 602 (colored red) showing through the transparent sides of the slider portion 202. As the color red is typically used to indicate danger, the user may be alerted to the fact that the needle tip 110 is not secure.

As the slider portion 202 is urged forward toward the needle tip 110, the color red may be continually visible on either side of the black strip 206, indicating continued danger resulting from the unsecured needle tip 110. In fact, the red color of the track surface 602 may be continually seen through transparent sides of the slider portion 202 until the lock element 108 engages the aperture 214 of the slider portion 202. At this point, and only at this point, the projection 606 may show through the aperture 214, and the black strip 206 may completely conceal the red color of the underlying track surface 602. As mentioned previously, the projection 606 may be painted green, indicating safety, such that the user perceives only the color green marked on all sides by black. In this manner, the user can be assured via visual feedback that the needle tip 110 has been properly secured and that the syringe 102 or other medical device is thus safe to handle.

As discussed above, in other embodiments, audible and/or tactile feedback may be used alone or in conjunction with visual feedback to enhance the perception of the user as to whether the needle tip 110 has been properly secured.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hypodermic needle shielding assembly comprising:
an adapter element having a proximal end and a distal end, said proximal end of said adapter element being configured for coupling to a syringe, and said distal end of said adapter element being configured for coupling to a hypodermic needle;
a track element mounted on said adapter element;
a guard element comprising a slider portion and a shield portion, said track element and said slider portion of said guard element being configured for slidable attachment to one another such that said guard element can be extended in a direction approximately parallel to the axis of said hypodermic needle from a retracted position in which the tip of said hypodermic needle is exposed, to a safety position in which the tip of said hypodermic needle is shielded by said shield portion of said guard element; and
a lock element configured to be in a loaded position when said guard element is in said retracted position, and in an engaged position when said guard element is in said safety position, so as to prevent said guard element from sliding relative to said track element when said lock element is in said engaged position;
wherein said hypodermic needle shielding assembly is configured to provide a visual feedback when said lock element is advanced from said loaded position to said engaged position, said visual feedback comprising at least one member selected from the group consisting of:
concealing a first color when said lock element is in said loaded position and revealing said first color when said lock element is in said engaged position; and
revealing a second color when said lock element is in said loaded position and concealing said second color when said lock element is in said engaged position.

2. The hypodermic needle shielding assembly of claim 1 further comprising an aperture formed through said slider portion of said guard element, said lock element being configured to engage said aperture when said lock element is in said engaged position.

3. The hypodermic needle shielding assembly of claim 2 wherein said lock element includes a projection, said projection and said aperture having an approximately equal shape such that said projection is received into said aperture when said lock element is in said engaged position.

4. The hypodermic needle shielding assembly of claim 3 further comprising a colored top surface of said projection, said colored top surface of said projection being visible through said aperture when said lock element is in said engaged position.

5. The hypodermic needle shielding assembly of claim 3 wherein said lock element further includes a biasing member that flexibly presses said projection against a bottom surface of said slider portion of said guard element when said lock element is in said loaded position, and that advances the projection into said aperture when said lock element is in said engaged position.

6. The hypodermic needle shielding assembly of claim 5 wherein said track element further includes a bracket coupled to said adapter element, said biasing member being attached at one end to said bracket and at another end to said projection.

7. The hypodermic needle shielding assembly of claim 4 further comprising a substantially opaque top surface of said slider portion of said guard element, said substantially opaque top surface of said slider portion of said guard element concealing said colored top surface of said projection when said lock element is in said loaded position.

8. The hypodermic needle shielding assembly of claim 7 wherein said colored top surface of said projection visually contrasts with said substantially opaque top surface of said slider portion of said guard element.

9. The hypodermic needle shielding assembly of claim 7 wherein said colored top surface of said projection is green.

10. The hypodermic needle shielding assembly of claim 7 wherein said substantially opaque top surface of said slider portion of said guard element is black.

11. The hypodermic needle shielding assembly of claim 1 wherein said track element includes a colored top surface of a substantially planar track surface, at least a portion of said colored top surface of said substantially planar track surface being visible through a substantially transparent portion of said slider portion of said guard element when said lock element is in said loaded position.

12. The hypodermic needle shielding assembly of claim 11 further comprising a substantially opaque top surface of said slider portion of said guard element, said substantially opaque top surface of said slider portion of said guard element concealing said colored top surface of said substantially planar track surface when said lock element is in said engaged position.

13. The hypodermic needle shielding assembly of claim 12 wherein said colored top surface of said substantially planar track surface visually contrasts with said substantially opaque top surface of said slider portion of said guard element.

14. The hypodermic needle shielding assembly of claim 12 wherein said colored top surface of said substantially planar track surface is red.

15. The hypodermic needle shielding assembly of claim 12 wherein said substantially opaque top surface of said slider portion of said guard element is black.

16. A hypodermic needle shielding assembly comprising:
an adapter element having a proximal end and a distal end, said proximal end of said adapter element being configured for coupling to a syringe, and said distal end of said adapter element being configured for coupling to a hypodermic needle;
a track element mounted on said adapter element;
a guard element comprising a slider portion and a shield portion, said track element and said slider portion of said guard element being configured for slidable attachment to one another such that said guard element can be extended in a direction approximately parallel to the axis of said hypodermic needle from a retracted position in which the tip of said hypodermic needle is exposed, to a safety position in which the tip of said hypodermic needle is shielded by said shield portion of said guard element;
an aperture formed through said slider portion of said guard element; and
a lock element configured to engage said aperture when said guard element is in said safety position, so as to prevent said guard element from sliding relative to said track element.

17. The hypodermic needle shielding assembly of claim 16 wherein said lock element includes a projection, said projection and said aperture having an approximately equal shape such that said projection is received into said aperture when said guard element is in said safety position.

18. The hypodermic needle shielding assembly of claim 17 wherein said lock element further includes a biasing member that flexibly presses said projection against a bottom surface of said slider portion of said guard element when said guard element is in said retracted position, and that advances said projection into said aperture when said guard element is in said safety position.

19. The hypodermic needle shielding assembly of claim 18 wherein said track element further includes a bracket coupled to said adapter element, said biasing member being attached at one end to said bracket and at another end to said projection.

20. The hypodermic needle shielding assembly of claim 19 wherein said shield portion of said guard element includes a channel.

21. The hypodermic needle shielding assembly of claim 20 wherein said channel and said biasing member are configured such that said channel can receive said biasing member when said guard element is in said retracted position.

22. The hypodermic needle shielding assembly of claim 16 further comprising:
   a slot formed along a length of said shield portion of said guard element, said slot being formed through the side of said shield portion that is opposite from said slider portion, said slot configured to receive a length of said hypodermic needle when said guard element is attached to said track element;
   wherein said slider portion of said guard element is substantially rigid.

23. A method for shielding a hypodermic needle comprising:
   providing an adapter element having a proximal end and a distal end, said proximal end of said adapter element being configured for coupling to a syringe, and said distal end of said adapter element being configured for coupling to a hypodermic needle;
   providing a track element mounted on said adapter element;
   providing a guard element comprising a slider portion and a shield portion, said track element and said slider portion of said guard element being configured for slidable attachment to one another;
   extending said guard element in a direction approximately parallel to the axis of said hypodermic needle from a retracted position in which the tip of said hypodermic needle is exposed to a safety position in which the tip of said hypodermic needle is shielded by said shield portion of said guard element; and
   advancing a lock element from a loaded position to an engaged position such that a visual feedback indicates that said guard element is prevented by said lock element from sliding relative to said track element;
   wherein said visual feedback comprises at least one member selected from the group consisting of:
      concealing a first color when said lock element is in said loaded position and revealing said first color when said lock element is in said engaged position; and
      revealing a second color when said lock element is in said loaded position and concealing said second color when said lock element is in said engaged position.

24. The method of claim 23 wherein concealing said first color comprises concealing a colored top surface of a projection of said lock element with a substantially opaque top surface of said slider portion of said guard element when said guard element is in said retracted position, and revealing said first color comprises revealing said colored top surface of said projection of said lock element through an aperture formed through said slider portion of said guard element when said lock element is in said engaged position.

25. The method of claim 24 wherein said colored top surface of said projection visually contrasts with said substantially opaque top surface of said slider portion of said guard element.

26. The method of claim 24 wherein said colored top surface of said projection is green.

27. The method of claim 24 wherein said substantially opaque top surface of said slider portion of said guard element is black.

28. The method of claim 23 wherein revealing said second color comprises revealing a colored top surface of a substantially planar track surface of said track element through a substantially transparent portion of said slider portion of said guard element when said lock element is in said loaded position, and concealing said second color comprises concealing said colored top surface of said substantially planar track surface of said track element with a substantially opaque top surface of said slider portion of said guard element when said lock element is in said engaged position.

29. The method of claim 28 wherein said colored top surface of said substantially planar track surface visually contrasts with said substantially opaque top surface of said slider portion of said guard element.

30. The method of claim 28 wherein said colored top surface of said substantially planar track surface is red.

31. The method of claim 28 wherein said substantially opaque top surface of said slider portion of said guard element is black.

32. A hypodermic needle shielding assembly comprising:
   an adapter element having a proximal end and a distal end, said proximal end of said adapter element being configured for coupling to a syringe, and said distal end of said adapter element being configured for coupling to a hypodermic needle;
   a track element mounted on said adapter element;
   a guard element comprising a slider portion and a shield portion, said track element and said slider portion of said guard element being configured for slidable attachment to one another such that said guard element can be extended in a direction approximately parallel to the axis of said hypodermic needle from a retracted position in which the tip of said hypodermic needle is exposed, to a safety position in which the tip of said hypodermic needle is shielded by said shield portion of said guard element; and
   a lock element configured to be in a loaded position when said guard element is in said retracted position, and in an engaged position when said guard element is in said safety position, so as to prevent said guard element from sliding relative to said track element when said lock element is in said engaged position;
   wherein said hypodermic needle shielding assembly is configured to provide a visual feedback when said lock element is advanced from said loaded position to said engaged position, said visual feedback comprising:
   concealing a first color and revealing a second color when said lock element is in said loaded position; and
   revealing said first color and concealing said second color when said lock element is in said engaged position.

* * * * *